(12) United States Patent
Lee et al.

(10) Patent No.: US 10,493,375 B2
(45) Date of Patent: Dec. 3, 2019

(54) DISTILLATION DEVICE

(71) Applicant: LG CHEM, LTD., Seoul (KR)

(72) Inventors: Sung Kyu Lee, Daejeon (KR); Joon Ho Shin, Daejeon (KR)

(73) Assignee: LG CHEM, LTD., Seoul (KR)

(*) Notice: Subject to any disclaimer, the term of this patent is extended or adjusted under 35 U.S.C. 154(b) by 79 days.

(21) Appl. No.: 15/579,507

(22) PCT Filed: Jun. 7, 2016

(86) PCT No.: PCT/KR2016/005981
§ 371 (c)(1),
(2) Date: Dec. 4, 2017

(87) PCT Pub. No.: WO2016/200111
PCT Pub. Date: Dec. 15, 2016

(65) Prior Publication Data
US 2018/0154278 A1    Jun. 7, 2018

(30) Foreign Application Priority Data

Jun. 8, 2015 (KR) .................. 10-2015-0080430

(51) Int. Cl.
*B01D 3/14* (2006.01)
*C07C 11/167* (2006.01)
*C07C 7/04* (2006.01)
*C07C 11/08* (2006.01)

(52) U.S. Cl.
CPC .............. *B01D 3/141* (2013.01); *C07C 7/04* (2013.01); *C07C 11/08* (2013.01); *C07C 11/167* (2013.01)

(58) Field of Classification Search
CPC .......... B01D 3/141; C07C 7/04; C07C 11/16; C07C 11/167
See application file for complete search history.

(56) References Cited

U.S. PATENT DOCUMENTS

2004/0045804 A1*   3/2004  Bohner .................. B01D 3/14
                                                          203/1
2006/0137967 A1    6/2006  Kister et al.
(Continued)

FOREIGN PATENT DOCUMENTS

| CN | 1708336 A | 12/2005 |
| JP | 2006-508797 A | 3/2006 |
| KR | 100795650 | 1/2008 |

(Continued)

OTHER PUBLICATIONS

Asprion, et al.: "Dividing wall columns: Fundamentals and recent advances", Chemical Engineering and Processing: Process Intensification, Elsevier, vol. 49, 2010, pp. 139-146.

*Primary Examiner* — Renee Robinson
(74) *Attorney, Agent, or Firm* — Dentons US LLP

(57) ABSTRACT

The present application relates to a distillation device and a distillation method, and according to the distillation device of the present application, it is possible to minimize the energy losses that occur in the refining process of the raw material containing the monomer and the solvent used in the polymerization process of the thermoplastic elastomer and to reduce the installation cost of the distillation device more than the case of refinement with two distillation columns, and thus the process economics may be improved.

6 Claims, 2 Drawing Sheets

(56) References Cited

U.S. PATENT DOCUMENTS

2010/0224536 A1* 9/2010 Schultz .................... B01D 3/14
    208/363
2011/0303526 A1* 12/2011 Lee ......................... B01D 3/14
    203/81

FOREIGN PATENT DOCUMENTS

KR      1020120076196     7/2012
WO     2014/112808 A1     7/2014

* cited by examiner

[Fig. 1]
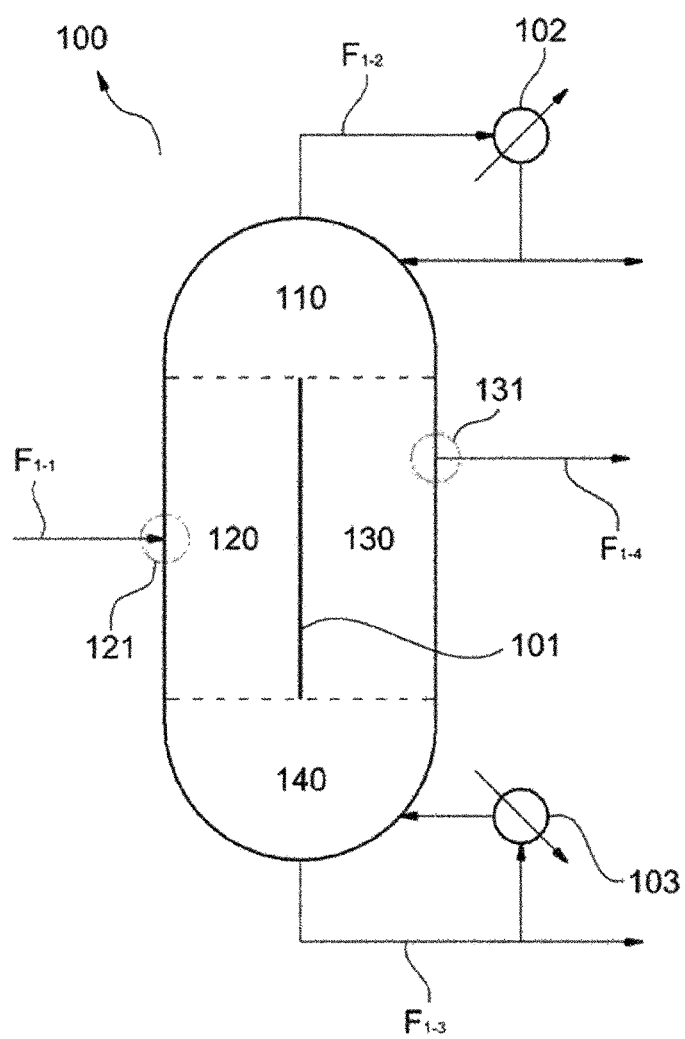

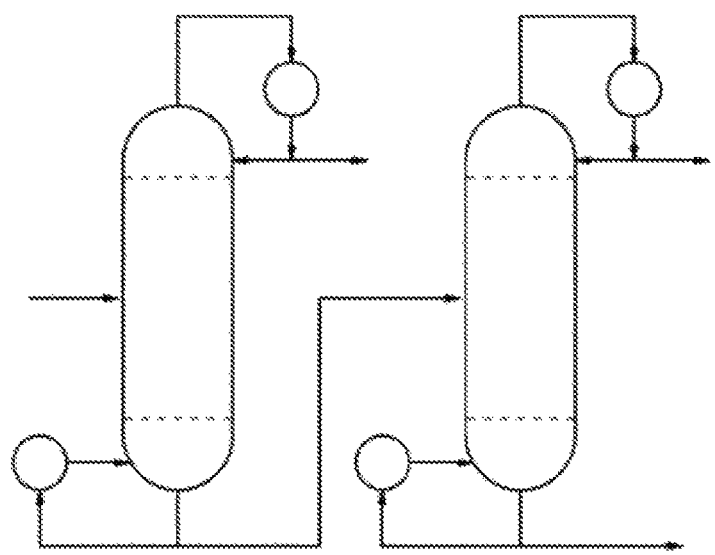
[Fig. 2] - RELATED ART

DISTILLATION DEVICE

This application is a National Stage Application of International Application No. PCT/KR2016/005981, filed Jun. 7, 2016, and claims the benefit of Korean Patent Application No. 10-2015-0080430, filed Jun. 8, 2015, the contents of which are incorporated herein by reference in their entirety for all purposes as if fully set forth below.

TECHNICAL FIELD

The present application relates to a distillation device and a method for separating a solvent and an unreacted monomer used in a polymerization process of thermoplastic elastomer in high purity and high energy efficiency.

BACKGROUND ART

The thermoplastic elastomer such as butadiene rubber has an excellent abrasion resistance, flexibility resistance and cold resistance, which is used for various applications in the chemical industry.

The butadiene rubber is polymerized by a solution polymerization method of dissolving 1,3-butadiene monomer in a solvent and then polymerizing it with a catalyst, and commercialized through a drying step after recovering the solvent from the polymerization solution. In the case of preparing the butadiene rubber via the solution polymerization method as above, a large quantity of solvent is used compared to the amount of monomer to be introduced, and thus there was a problem that a large amount of energy is consumed in the process for recovering the solvent and the unreacted monomer after polymerization. Conventionally, the solvent and the unreacted monomer were recovered from the polymerization solution containing the solvent and the unreacted monomer after solution polymerization with a distillation device sequentially connected by two distillation columns, but there was a problem that a large amount of energy is consumed.

Therefore, the process of recovering solvents is required, which is capable of reducing the installation cost of the distillation device and separating high purity compounds.

DETAILED DESCRIPTION OF INVENTION

Technical Problem

It is an object of the present application to provide a distillation device for separating a solvent and an unreacted monomer used in a polymerization process of thermoplastic elastomer in high purity and high energy efficiency.

Technical Solution

The present application relates to a distillation device. According to the distillation devices in accordance with exemplary embodiments of the present application, the energy loss occurring in a refining process of raw materials containing a monomer, such as $C_4$ fraction, and a solvent, for example $C_6$ fraction, used in polymerization processes of thermoplastic elastomers, may be minimized, and also, according to the distillation device of the present application, it is possible to prevent from discharging $C_4$ fraction components in a product outflow region, as a part of the $C_6$ fraction is effused from top and bottom regions of a dividing wall distillation column. In addition, the distillation device of the present application can provide temperature and pressure conditions inside the distillation column for effusing $C_6$ fractions in a specific content range as above, where the solvent and the unreacted monomer used in the polymerization process of thermoplastic elastomer using the distillation device of the present application may be separated in high purity and high energy efficiency and re-used.

Hereinafter, the distillation device of the present application is explained with reference to the drawings, but the drawings are illustrative, whereby the scope of the distillation device is not limited to the attached drawings.

FIG. 1 is a drawing illustratively showing the distillation device in accordance with embodiments of the present application.

As shown in FIG. 1, the distillation device of the present application includes a distillation column (100) equipped with a condenser (102), a reboiler (103) and a dividing wall (101). The distillation column (100) above may be a dividing wall distillation column (100). The dividing wall distillation column (100) is a device devised for distillation of raw materials ($F_{1-1}$) comprising three components having a low-boiling point and a mid-boiling point and a high-boiling point, which is a device similar to so-called thermally coupled distillation column (Petlyuk column) in thermodynamic aspect. The thermally coupled distillation column is designed to primarily separate low- and high-boiling materials in a pre-separator and to separate low-, mid- and high-boiling materials in a main separator, respectively by introducing the top part and the bottom part in the pre-separator into feed ends of the main separator, respectively. In contrast, the dividing wall distillation column (100) is a type that integrates the pre-separator inside the main separator by installing the dividing wall (101) within the column.

Furthermore, in the case of the dividing wall distillation column (100), flexibility for operating condition change is lowered due to the structural characteristics which cannot control the internal circulation flow rate when the design is determined, unlike the Petlyuk distillation column, and thus an exact simulation for various disturbances and a determination of easily controllable control structure at the early design stage of the distillation column are required, further, in the dividing wall distillation column (100), information on design structures and operating conditions such as position of feed ends, dividing wall section setting, production end position of mid-boiling material, total number of theoretical stages, distillation temperature and distillation pressure are not only very limited, but particularly design structures such as number of stages of distillation column, position of feed ends and outflow ends and operating conditions such as distillation temperature, pressure and reflux ratio should be specially changed depending on characteristics of a subject material to be distilled. As described above, the distillation device of the present application can provide operating conditions of the dividing wall distillation column (100) suitably designed for separating the solvent and the unreacted monomer used in the polymerization process of thermoplastic elastomers in high purity and high energy efficiency so as to be capable of saving energy and reducing the installation cost.

Specific kind of the dividing wall distillation column (100) that can be used in the distillation device of the present application is not particularly limited. For example, the dividing wall distillation column (100) having a general structure as shown in FIG. 1 is used, or considering the refining efficiency, the distillation column designed to change position and shape of the dividing wall (101) in the distillation column may be also used. In addition, the number of stages the inner diameter of the distillation column, and the like are also not particularly limited and, for example, can be set based on the number of theoretical stages derived from the distillation curve considering the composition of the raw material ($F_{1-1}$), and the like.

In one example, the dividing wall distillation column (100) of the present application may have the same structure as that of FIG. 1. As shown in FIG. 1, in an exemplary dividing wall distillation column (100), the inside may be separated by the dividing wall (101). In addition, the inside of the dividing wall column (100), as separated by virtual dashed lines in FIG. 1, may be sectionalized into the middle region comprising the dividing wall (101) and the top region and the bottom region not including the dividing wall (101). In addition, the middle region can be sectionalized into the raw material feed zone (120) and the product outflow zone (130) divided by the dividing wall (101). For example, the dividing wall distillation column (100) may be sectionalized into the top region (110) from which the low-boiling flow is discharged, the bottom region (140) from which the high-boiling flow is discharged, the raw material feed zone (120) to which the raw material ($F_{1-1}$) is introduced and the product outflow zone (130) from which the product is effused. The "top" of the dividing wall distillation column (100) means the highest portion of the column of the dividing wall distillation column (100), which may be included in the upper region of the above described dividing wall distillation column (100), and the "bottom" of the dividing wall distillation column (100) means the lowest portion of the column of the dividing wall distillation column (100), which may be included in the lower region of the above described dividing wall distillation column (100). Unless specifically defined otherwise in this specification, the upper region is used in the same meanings as the top region (110), and the lower region is used in the same meanings as the bottom region (140). The "condenser" is a device separately installed from the distillation column, which may refer to a device for cooling in a manner such that the material effused from the main body is contacted with the cooling water introduced from the outside. For example, the condenser (102) of the distillation device may be a device for condensing the top flow ($F_{1-2}$) effused from the top region (110) of the dividing wall distillation column (100). In addition, the "reboiler" is a heating device installed outside the distillation column, which may refer to a device for heating and evaporating the high-boiling flow again. For example, the reboiler (103) of the distillation device can be a device for heating the bottom flow ($F_{1-3}$) effused from the bottom region (140) of the dividing wall distillation column (100).

In the dividing wall distillation column (100) of the present application, the raw material feed region (120) and the product outflow region (130) may be separated or isolated to each other by the dividing wall (101). Accordingly, it is possible to prevent from mixing the flow in the raw material feed region (120) and the flow in the product outflow region (130) each other. The term "separation or isolation" herein means that the flow in each region flows or present in the region divided by the dividing wall (101). In one example, the dividing wall (101) of the dividing wall distillation column (100) is included in the middle region of the dividing wall distillation column (100). Specifically, the dividing wall (101), as calculated based on the number of theoretical stages of the dividing wall distillation column (100), may be located in 40 to 60%, preferably 42 to 55%, and more preferably 44% to 50% of the total number of theoretical stages calculated on the basis of the top. The "number of theoretical stages" above means the number of virtual regions or stages in which two phases such as a vapor phase and a liquid phase achieve equilibrium with each other in the dividing wall distillation column (100). By including the dividing wall (101) in the above range inside the dividing wall distillation column (100), it can be effectively blocked that the flow in the raw material feed region (120) and the flow in the product outflow region (130) are mixed. In addition, it can be prevented that the low-boiling component is mixed in the product flow ($F_{1-4}$) effused from the product outflow region (130) to be effused.

In one embodiment of the present application, the dividing wall distillation column (100) includes a raw material feed port (121) located in the raw material feed region (120), where the raw material ($F_{1-1}$) comprising $C_4$ fractions and $C_6$ fractions flows into the raw material feed port (121).

In one example, the $C_4$ fraction is a monomer component used in polymerizing thermoplastic elastomers, in particular, the unreacted monomer after polymerization, which may include one or more selected from the group consisting of 1,3-butadiene, 1-butene, n-butane, iso-butane, trans-2-butene and cis-2-butene, without being limited thereto. In one embodiment, when the thermoplastic elastomer is a butadiene rubber, the $C_4$ fraction may be 1,3-butadiene. Also, the $C_6$ fraction is a solvent component in which the monomer is dissolved, which may include one or more selected from the group consisting of n-hexane, c-hexane and iso-hexane, without being limited thereto. For example, if the thermoplastic elastomer is a butadiene rubber, the $C_6$ fraction may be n-hexane.

For example, the raw material ($F_{1-1}$) containing $C_4$ fraction and $C_6$ fraction is introduced into the raw material feed port (121) located in the raw material feed zone (120) of the dividing wall distillation column (100), and the introduced raw material ($F_{1-1}$) is divided into the bottom flow ($F_{1-3}$) effused from the bottom region (140), the top flow ($F_{1-2}$) effused from the top region (110) and the product flow ($F_{1-4}$) effused from the product outflow port (131) located in the product outflow zone (130), respectively and effused.

From the top region (110) of the dividing wall distillation column (100) the top flow ($F_{1-2}$), the relatively low-boiling component, of the components included in the raw material ($F_{1-1}$) may be effused, and from the bottom region (140) of the dividing wall distillation column (100) the bottom flow ($F_{1-3}$), the relatively high-boiling component, of the components included in the raw material ($F_{1-1}$) may be effused. From the product outflow zone (130) of the dividing wall distillation column (100) the product flow ($F_{1-4}$), the relatively mid-boiling component, of the components included in the raw material ($F_{1-1}$) may be effused. The "low-boiling flow" above means a flow that the relatively low-boiling component is rich among the raw material flow comprising three components of low-boiling, mid-boiling and high-boiling components and the low-boiling flow means, for example, the flow effused from the top region (110) of the dividing wall distillation column (100). The "high-boiling flow" above means a flow that the relatively high-boiling component is rich among the raw material flow comprising three components of low-boiling, mid-boiling and high-boiling components and the high-boiling flow means, for example, the flow that the relatively high-boiling component is rich, effused from the bottom region (140) of the dividing wall distillation column (100). The "mid-boiling flow" above means a flow that the component having a boiling point between the low-boiling component and the high-boiling component is rich among the raw material flow comprising three components of low-boiling, mid-boiling and high-boiling components and the mid-boiling flow means, for example, the flow effused from the product outflow port (131) of the product outflow zone (130) of the dividing wall distillation column (100). The terms "rich flow" above means a flow that each content of the low-boiling component included in the flow effused from the top region (110), the high-boiling component included in the flow effused from the bottom region (140) and the mid-boiling component included in the flow effused from the product outflow zone (130), of the dividing wall distillation column (100), is higher than each content of the low-boiling component, the high-boiling component and the mid-boiling component included in the raw material ($F_{1-1}$). For example, it can mean the flow having each content of 50% by weight or more, 80% by weight or more, 90% by weight or more, 95% by weight or more or 99% by weight or more, which is represented by the low-boiling component included in the top flow ($F_{1-2}$), the high-boiling component included in the bottom flow ($F_{1-3}$) and the mid-boiling component included in the product flow ($F_{1-4}$), of the dividing wall distillation column (100). In this specification, the low-boiling flow and the top flow ($F_{1-2}$) of the dividing wall column (100) may be used in the same meanings, the high-boiling flow and the bottom flow ($F_{1-3}$) of the dividing wall distillation column (100) may be used in the same meanings, and the mid-boiling flow and the product flow ($F_{1-4}$) of the dividing wall distillation column (100) may be used in the same meanings.

The dividing wall distillation column (100) includes the product outflow port (131), from which the product flow is effused. The product outflow port (131) may be located at the product outflow zone (130) of the dividing wall distillation column (100), for example, higher than the raw material feed port (121), that is above. In one example, when the number of theoretical stages is calculated on the basis of the top, the raw material feed port (121) may be located in 55 to 85%, 55 to 84% or 60 to 85% of the total number of theoretical stages calculated on the basis of the top. Furthermore, when the number of theoretical stages is calculated on the basis of the top, the product outflow port (131) may be located in 40 to 55%, 43 to 55% or 40 to 50% of the total number of theoretical stages calculated on the basis of the top. For example, if the number of theoretical stages of the dividing wall distillation column (100) is 100 stages, the first stage of the dividing wall distillation column (100) is the top, the one hundredth stage corresponds to the bottom, the raw material feed port (121) may be located in 55 to 85 stages, and the product outflow port (131) may be located in 40 to 55 stages. As the product outflow port (131) is located higher than the raw material feed port (121) as above, the gas/liquid contact section of the $C_6$ fraction with the component having higher boiling point than the $C_6$ fraction, which has the greatest impact on the purity of the $C_6$ fraction obtained from the product outflow region, may be lengthened to obtain the effect of improving the separation efficiency of the $C_6$ fraction.

In order to perform the separation process from the raw material ($F_{1-1}$) containing three components having low-, mid- and high-boiling points, the raw material ($F_{1-1}$) is introduced into the raw material feed port (121) of the raw material feed zone (120) of the dividing wall distillation column (100) as in FIG. 1. The raw material ($F_{1-1}$) containing the $C_4$ fraction and the $C_6$ fraction introduced into the raw material feed port (121) of the raw material feed zone (120) may be divided into the bottom flow ($F_{1-3}$) containing the fraction having higher boiling point than the $C_6$ fraction, for example, a dimer of the $C_4$ fraction and a trimer of the $C_4$ fraction, the top flow ($F_{1-2}$) containing the $C_4$ fraction, for example, 1,3-butadiene and the product flow ($F_{1-4}$) containing the $C_6$ fraction, for example, n-hexane and effused. The bottom flow ($F_{1-3}$) effused from the bottom region (140) of the dividing wall distillation column (100) may pass through the reboiler (103), and some or all of the bottom flow ($F_{1-3}$) passing through the reboiler (103) may be introduced into the bottom region (140) to be refluxed into the dividing wall distillation column (100) or stored as the product. In addition, the top flow ($F_{1-2}$) effused from the top region (110) of the dividing wall distillation column (100) may pass through the condenser (102), and some or all of the top flow ($F_{1-2}$) passing through the condenser (102) may be introduced into the top region (110) to be refluxed into the dividing wall distillation column (100) or stored as the product and the product flow ($F_{1-4}$) effused from the product outflow port (131) of the product outflow zone (130) of the dividing wall distillation column (100) may be stored as the product.

In one embodiment, in the distillation device of the present application, a part of the C6 fraction included in the product flow ($F_{1-4}$) may be included in the top flow and the bottom flow to be effused. For example, if the raw material ($F_{1-1}$) containing the $C_4$ fraction and the $C_6$ fraction is introduced into the raw material feed port (121) of the dividing wall distillation column (100), the introduced raw material may be divided into the bottom flow ($F_{1-3}$) containing the $C_6$ fraction and the fraction having higher boiling point than the $C_6$ fraction, the top flow ($F_{1-2}$) containing the $C_4$ fraction and the $C_6$ fraction and the product flow ($F_{1-4}$) containing the $C_6$ fraction to be effused. In one example, in the distillation device of the present application, the content of the $C_6$ fraction in the top flow ($F_{1-2}$) may be adjusted in 1 to 20 parts by weight relative to the total components included in the top flow ($F_{1-2}$) and the content of the $C_6$ fraction in the bottom flow ($F_{1-3}$) may be adjusted in 85 to 95 parts by weight relative to the total components included in the bottom flow ($F_{1-3}$), whereby the recovery rate may be increased as well as high purity $C_6$ fraction may be separated in an excellent separation efficiency. That is, by adjusting the content of the $C_6$ fraction included in the top flow ($F_{1-2}$) and the bottom flow ($F_{1-3}$) as described above, the $C_6$ fraction effused into the product flow, for example, n-hexane may be effectively separated and the energy savings may be maximized. In addition, as the $C_6$ fraction is partly effused from the top region and the bottom region of the dividing wall distillation column as above, it is possible to prevent the discharge of the $C_4$ fraction component in the product outflow zone.

In one example, the content of the $C_6$ fraction in the top flow ($F_{1-2}$) may be 1 to 20 parts by weight, for example, 3 to 18 parts by weight, 5 to 16 parts by weight, 7 to 20 parts by weight or 8 to 14 parts by weight relative to the total components included in the top flow ($F_{1-2}$) and the content of the $C_6$ fraction in the bottom flow ($F_{1-3}$) may be 85 to 95 parts by weight, for example, 85 to 94 parts by weight, 85 to 93 parts by weight, 85 to 92 weight parts or 85 to 90 parts by weight relative to the total components included in the bottom flow ($F_{1-3}$). For example, the content of n-hexane in the top flow ($F_{1-2}$) may be 1 to 20% by weight, for example, 3 to 18% by weight, 5 to 16% by weight, 7 to 20% by weight or 8 to 14% by weight and the content of n-hexane in the bottom flow ($F_{1-3}$) may be 85 to 95% by weight, for example, 85 to 94% by weight, 85 to 93% by weight, 85 to 92% by weight or 85 to 90% by weight, where the content of 1,3-butadiene in the top flow ($F_{1-2}$) of the dividing wall distillation column (100) may be 1% by weight or less, 3% by weight or less, or 5% by weight, and the content of n-hexane in the product flow ($F_{1-4}$) of the dividing wall distillation column (100) may be 85% by weight or more, 87% by weight or more, or 88% by weight.

Hereinafter, the process of separating butadiene mixtures and n-hexane using the distillation device according to one embodiment of the present application will be described in more detail.

In one example, the raw material ($F_{1-1}$) containing the $C_4$ fraction and the $C_6$ fraction is into the raw material feed port (121) of the dividing wall distillation column (100). In this case, from the top region (110) of the dividing wall column (100) the top flow ($F_{1-2}$), such as the flow containing some of the $C_6$ fraction of the raw material ($F_{1-1}$) and the $C_4$ fraction of the relatively low-boiling component, for example the flow containing 1,3-butadiene and n-hexane may be effused, and the effused top flow ($F_{1-2}$) passes through the condenser (102), so that some may be refluxed into the top region (110) of the dividing wall distillation column (100) and the remaining portion may be stored as the product. Furthermore, from the bottom region (140) of the dividing wall distillation column (100) the bottom flow ($F_{1-3}$) containing some of the $C_6$ fraction of the raw material ($F_{1-1}$) and the component having higher boiling point than the $C_6$ fraction of the relatively high-boiling component, for example the flow containing the dimer of the $C_4$ fraction and the trimer of the $C_4$ fraction may be effused, and the effused bottom flow ($F_{1-3}$) passes through the reboiler (103), so that some may be refluxed into the bottom region (140) of the dividing wall distillation column and the remaining portion may be stored as the product. In addition, from the product outflow port (131) of the product outflow zone (130) of the dividing wall distillation column (100) the product flow ($F_{1-4}$) containing the $C_6$ fraction of the mid-boiling component of the raw material ($F_{1-1}$), for example, n-hexane-rich flow may be separated and effused.

When the raw material ($F_{1-1}$) containing the $C_4$ fraction and the $C_6$ fraction is separated using the distillation device of the present application as above, in order to effuse the $C_6$ fraction in a specific content range from the top region and the bottom region, temperature and pressure conditions inside the distillation column may be controlled in a specific range.

In one example, the pressure of the top region (110) of the dividing wall distillation column (100) may be 3.5 $kg/cm^2g$ to 4.5 $kg/cm^2g$, for example, 3.6 $kg/cm^2g$ to 4.4 $kg/cm^2g$, or 3.7 to 4.3 $kg/cm^2g$ and the pressure of the bottom region (140) of the dividing wall distillation column (100) may be 3.63 to 4.7 $kg/cm^2g$, for example, 3.65 $kg/cm^2g$ to 4.6 $kg/cm^2g$, or 3.67 $kg/cm^2g$ to 4.5 $kg/cm^2g$.

In addition, the temperature of the top region (110) of the dividing wall distillation column (100) may be of 45° C. to 60° C., 47° C. to 58° C., or 49° C. to 56° C. and the temperature of the bottom region (140) of the dividing wall distillation column (100) may be 120° C. to 140° C., 122° C. to 138° C., or 124° C. to 136° C.

The reflux ratio of the top flow ($F_{1-2}$) refluxed into the top region (110) of the dividing wall distillation column (100) among the top flow ($F_{1-2}$) of the dividing wall distillation column (100) may be 4.5 to 8.0, and preferably 4.6 to 5.8, or 4.8 to 5.6 in view of thermodynamics. The "reflux ratio" above means a ratio of the refluxed flow rate (kg/hr) relative to the outflow flow rate (kg/hr) effused from the distillation column (100).

The present application also relates to a distillation method of separating a solvent and an unreacted monomer used in a polymerization process of thermoplastic elastomer in high purity and high energy efficiency.

An exemplary distillation method of the present application can be carried out by using the above described distillation device, where the contents overlapped with the contents described in the aforementioned distillation device will be omitted.

In one embodiment of the distillation method of the present application, it comprises a raw material inflow step of introducing a raw material ($F_{1-1}$) and a distillation step of separating the raw material ($F_{1-1}$).

The step of introducing the raw material ($F_{1-1}$) is a step of introducing the raw material ($F_{1-1}$) containing the $C_4$ fraction and the $C_6$ fraction into the dividing wall distillation column (100), and more specifically, the raw material feed zone (120) of the dividing wall distillation column (100) that the inside is provided with a dividing wall (101), the inside is sectionalized into the top region (110) and the bottom region (140), not located by the dividing wall (101), and the middle region located by the dividing wall (101), and the middle region is sectionalized into the raw material feed zone (120) and the product outflow zone (130) divided by the dividing wall (101).

The distillation step of separating the material ($F_{1-1}$) is a step that the raw material ($F_{1-1}$) introduced into the raw material feed zone (120) is separated and effused from the top region (110), the product outflow zone (130) and the bottom region (140) of the dividing wall distillation column (100), respectively, and more specifically, a step that the $C_4$ fraction and the $C_6$ fraction are separated and effused from the top region (110) of the distillation column (100), the $C_6$ fraction is separated and effused from the product outflow zone (130) of the distillation column, and the $C_6$ fraction and the fraction having higher boiling point than the $C_6$ fraction are separated and effused from the bottom region (140) of the distillation column.

Explanation for the raw material ($F_{1-1}$) containing the $C_4$ fraction and the $C_6$ fraction is the same as described above, and thus will be omitted.

In one example, the distillation step may comprise adjusting the content of the $C_6$ fraction in the top flow ($F_{1-2}$) in 1 to 20 parts by weight, for example, 3 to 18 parts by weight, 5 to 15 parts by weight, 7 to 20 parts by weight or 8 to 14 parts by weight relative to the total components included in the top flow ($F_{1-2}$) and adjusting the content of the $C_6$ fraction in the bottom flow ($F_{1-3}$) in 85 to 95 parts by weight, for example, 85 to 94 parts by weight, 85 to 93 parts by weight, 85 to 92 parts by weight or 85 to 90 parts by weight relative to the total components included in the bottom flow ($F_{1-3}$), whereby high purity $C_6$ fraction may be separated in high efficiency. That is, by adjusting the contents of the fractions contained in the top flow ($F_{1-2}$) and the bottom flow ($F_{1-3}$), the $C_6$ fraction effused into the product flow, for example n-hexane may be effectively separated and the energy saving effect may be maximized.

The detailed explanations for the pressure, the temperature, and the reflux ratio of the top flow ($F_{1-2}$) effused from the top region (110), the bottom flow ($F_{1-3}$) effused from the bottom region (140) and the product flow ($F_{1-4}$) effused from the product outflow zone (130), of the dividing wall distillation column (100), are the same as described in the aforementioned dividing wall distillation column (100), and thus will be omitted.

Because each of the above steps is organically combined, each boundary is not clearly distinguished according to the order of time, whereby each of the above steps may be carried out sequentially or each independently at the same time. In addition, the method may further comprise process steps that can be typically performed in the art to which the present invention belongs before or after each of the above steps, and thus is not limited to only the above steps.

According to the distillation device of the present application and the distillation method using the same, the energy consumption volume is reduced and the size of the distillation device used in refining the raw material is also minimized to reduce energy consumption, whereby the process economics may be improved.

Effects of Invention

According to the distillation device of the present application, it is possible to minimize the energy losses that occur in the refining process of the raw material containing the monomer and the solvent used in the polymerization process of the thermoplastic elastomer and to reduce the installation cost of the distillation device more than the case of refinement with two distillation columns, and thus the process economics may be improved.

BRIEF DESCRIPTION OF DRAWINGS

FIG. 1 is a diagram illustratively showing the distillation device according to embodiments and examples of the present application.

FIG. 2 is a diagram schematically showing the distillation device used in a comparative example.

BEST MODE FOR CARRYING OUT INVENTION

Hereinafter the present invention is explained in more detail through examples according to the present invention and a comparative example not according to the present invention, but the scope of the present invention is not limited by examples as set forth below.

Example 1

A butadiene mixture and n-hexane were separated using the distillation device of FIG. 1. Specifically, 93 raw material containing 1,3-butadiene and n-hexane was introduced at a flow rate of 21,269 kg/hr into the raw material feed port located at Stage 19 of the dividing wall distillation column having a number of theoretical stages of 30 stages to perform a separation process, and each flow was effused from the top region, the product outflow region and the bottom region, of the dividing wall distillation column.

At this time, some of the top flow effused at a flow rate of 4,179 kg/hr from the top region of the dividing wall distillation column was refluxed via the condenser into the dividing wall distillation column and the remaining portion was separated as the product containing 1,3-butadiene, and some of the bottom flow effused at a flow rate of 33 kg/hr from the bottom region was refluxed via the reboiler into the dividing wall distillation column and the remaining portion was stored in a fuel storage tank for utilizing as a fuel for high-boiling component. Furthermore, the product flow effused at a flow rate of 20,562 kg/hr from the product outflow zone was effused from the product outflow port located at Stage 15 of the dividing wall distillation column having a number of theoretical stages of 30 stages and separated, and separated and stored as the product containing n-hexane. In addition, the operating pressure of the top region of the dividing wall distillation column was adjusted to 4.0 $kg/cm^2g$ to 4.1 $kg/cm^2g$, the operation temperature was adjusted to 56° C. to 59° C., the operating pressure of the bottom region was adjusted to 4.15 $kg/cm^2g$ to 4.25 $kg/cm^2g$, and the operation temperature was adjusted to 129° C. to 132° C. In addition, the operating pressure of the product outflow zone was adjusted to 4.1 $kg/cm^2g$ to 4.2 $kg/cm^2g$, and the operation temperature was adjusted to 125° C. to 127° C. The reflux ratio of the top region of the dividing wall distillation column was set to 5.8 to 6.4.

The content of the $C_6$ fraction in the top flow was adjusted to 9.9 parts by weight relative to the total components contained in the top flow, and the content of the $C_6$ fraction in the bottom flow was adjusted to 85 parts by weight relative to the total components contained in the bottom flow.

Example 2

1,3-Butadiene and n-hexane were separated in the same manner as Example 1 except that the operating pressure of the top region of the dividing wall column was adjusted to 3.6 $kg/cm^2g$ to 3.7 $kg/cm^2g$, the operating temperature was adjusted to 54° C. to 58° C., the operating pressure of the bottom region was adjusted to 3.85 $kg/cm^2g$ to 3.95 $kg/cm^2g$, the operation temperature was adjusted to 123° C. to 125° C., the operation pressure of the product outflow zone was adjusted to 3.7 $kg/cm^2g$ to 3.8 $kg/cm^2g$, and the operation temperature was adjusted to 123° C. to 125° C. In addition, the reflux ratio of the top region of the dividing wall distillation column was set to 5.6 to 6.2.

In this case, the content of the $C_6$ fraction in the top flow was adjusted to 9.9 parts by weight relative to the total components contained in the top flow, and the content of the $C_6$ fraction in the bottom flow was adjusted to 85 parts by weight relative to the total components contained in the bottom flow.

Example 3

1,3-Butadiene and n-hexane were separated in the same manner as Example 1 except that the operating pressure of the top region of the dividing wall column was adjusted to 4.3 $kg/cm^2g$ to 4.4 $kg/cm^2g$, the operating temperature was adjusted to 60° C. to 63° C., the operating pressure of the bottom region was adjusted to 4.55 $kg/cm^2g$ to 4.65 $kg/cm^2g$, the operation temperature was adjusted to 129° C. to 132° C., the operation pressure of the product outflow zone was adjusted to 4.4 $kg/cm^2g$ to 4.5 $kg/cm^2g$, and the operation temperature was adjusted to 129° C. to 132° C. In addition, the reflux ratio of the top region of the dividing wall distillation column was set to 7.0 to 7.5.

In this case, the content of the $C_6$ fraction in the top flow was adjusted to 9.9 parts by weight relative to the total components contained in the top flow, and the content of the $C_6$ fraction in the bottom flow was adjusted to 85 parts by weight relative to the total components contained in the bottom flow.

Example 4

1,3-Butadiene and n-hexane were separated in the same manner as Example 1 except that the dividing wall distillation column was used, in which the raw material feed port was located at Stage 25 of the dividing wall distillation column having a number of theoretical stages of 30 stages and the product outflow port was located at Stage 13 of the dividing wall distillation column having a number of theoretical stages of 30 stages.

In this case, the content of the $C_6$ fraction in the top flow was adjusted to 9.9 parts by weight relative to the total components contained in the top flow, and the content of the $C_6$ fraction in the bottom flow was adjusted to 85 parts by weight relative to the total components contained in the bottom flow.

Example 5

1,3-Butadiene and n-hexane were separated in the same manner as Example 1 except that the dividing wall distillation column was used, in which the raw material feed port was located at Stage 15 of the dividing wall distillation column having a number of theoretical stages of 30 stages and the product outflow port was located at Stage 19 of the dividing wall distillation column having a number of theoretical stages of 30 stages.

In this case, the content of the $C_6$ fraction in the top flow was adjusted to 9.9 parts by weight relative to the total components contained in the top flow, and the content of the $C_6$ fraction in the bottom flow was adjusted to 85 parts by weight relative to the total components contained in the bottom flow.

Comparative Example 1,3-Butadiene and n-hexane were separated using the distillation device connected by two distillation columns as in FIG. 2. Specifically, 138 raw material containing 1,3-butadiene and n-hexane was introduced at a flow rate of 21,269 kg/hr into the first distillation column to perform the separation process.

The low-boiling flow discharged at a flow rate of 1,451 kg/hr from the top region of the first distillation column passed through the condenser, and then some was refluxed into the first distillation column and the remaining portion was stored as the product, and some of the flow discharged at a flow rate of 20,615 kg/hr from the bottom region of the first distillation column passed through the reboiler, and then some was again refluxed into the bottom region of the first distillation column and the remaining portion was introduced into the second distillation column. The mid-boiling flow discharged from the top of the second distillation column at a flow rate of 25,867 kg/hr was condensed with the condenser, and then some was again refluxed into the top region of the second distillation column and the remaining portion was separated as the product, and the high-boiling flow discharged from the bottom of the second distillation column at a flow rate of 23 kg/hr passed through the reboiler, and then some was again refluxed into the bottom region of the second distillation column and the remaining portion was separated as the product. In this case, the temperature of the top of the first distillation column was adjusted to 45° C. to 65° C., the pressure was adjusted to 3.5 kg/cm²g to 4.5 kg/cm²g, the temperature of the bottom was adjusted to 120° C. to 140° C., the pressure was adjusted to 3.71 kg/cm²g to 4.71 kg/cm²g, the temperature of the top of the second distillation column was adjusted to 75° C. to 95° C., the pressure was adjusted to 0.24 kg/cm²g to 0.91 kg/cm²g, the temperature of the bottom was adjusted to 92° C. to 107° C., and the pressure was adjusted to 0.4 kg/cm²g to 10.7 kg/cm²g. In addition, the reflux ratio of the top region of the first distillation column was set to 0.50 to 0.60, and the reflux ratio of the top region of the second distillation column was set to 0.15 to 0.25.

After purifying the raw material containing the butadiene mixtures and n-hexane according to the examples and comparative example above, the purity of the butadiene mixtures and n-hexane, and energy consumption volumes were measured and represented in Table 1 below.

TABLE 1

|  | Comparative Example | Example 1 | Example 2 | Example 3 | Example 4 | Example 5 |
|---|---|---|---|---|---|---|
| Total energy consumption (MMKcal/hr) | 2.16 | 1.00 | 0.98 | 1.40 | 1.27 | 2.10 |
| Savings (MMKcal/hr) | 0.00 | 1.16 | 1.18 | 0.76 | 0.89 | 0.06 |
| Energy saving ratio (%) | — | 53.7 | 54.6 | 35.2 | 41.2 | 2.8 |
| Purity of product    1,3-butadiene | 84.8 | 84.8 | 84.8 | 84.8 | 84.8 | 84.8 |
| Purity of product    n-hexane | 99.8 | 99.8 | 99.8 | 99.8 | 99.8 | 99.8 |
| Content of $C_6$ fraction in top flow (part by weight) | — | 9.9 | 9.9 | 9.9 | 9.9 | 9.9 |
| Content of $C_6$ fraction in bottom flow (part by weight) | — | 85 | 85 | 85 | 85 | 85 |

As shown in Table 1, it can be confirmed that the total amount of energy used in the purification process using the distillation device of the examples of the present application decreased in terms of the total energy consumption compared to the total amount of energy used in the purification process using the distillation device of the comparative example. That is, when 1,3-butadiene and n-hexane are separated by the distillation device according to examples of the present application, the effect of energy savings of at most 54.6% can be obtained as compared to the case using the distillation device of the comparative example.

The invention claimed is:

1. A distillation method comprising
   a raw material inflow step of introducing a raw material containing a $C_4$ fraction and a $C_6$ fraction into a raw material feed zone of a dividing wall distillation column that the inside is provided with a dividing wall, said inside is sectionalized into a top region and a bottom region, such that said dividing wall does not extend into the top region and the bottom region, and a middle region comprising said dividing wall, and said middle region is sectionalized into said raw material feed zone and a product outflow zone divided by said dividing wall; and
   a distillation step that said $C_4$ fraction and a first portion of said $C_6$ fraction are separated and effused from the top region of said distillation column, a second portion of said $C_6$ fraction is separated and effused from the product outflow zone of said distillation column, and a third portion of said $C_6$ fraction and a fraction having a higher boiling point than said $C_6$ fraction are separated and effused from the bottom region of said distillation column, wherein said distillation step comprises adjusting the content of the first portion of said $C_6$ fraction in said top flow in 1 to 20 parts by weight relative to the total components included in said top flow and adjusting the content of the third portion of said $C_6$ fraction in said bottom flow in 85 to 95 parts by weight relative to the total components included in said bottom flow.

2. The method according to claim 1, comprising adjusting the pressure of the top region to 3.5 to 4.5 $kg/cm^2g$.

3. The method according to claim 1, comprising adjusting the temperature of the top region to 45° C. to 60° C.

4. The method according to claim 1, comprising adjusting the pressure of the bottom region to 3.63 to 4.7 $kg/cm^2g$.

5. The method according to claim 1, comprising adjusting the temperature of the bottom region to 120° C. to 140° C.

6. The method according to claim 1, comprising adjusting the reflux ratio of the top region to 4.0 to 8.0.

* * * * *